(12) United States Patent
Lu et al.

(10) Patent No.: US 7,567,694 B2
(45) Date of Patent: Jul. 28, 2009

(54) METHOD OF PLACING CONSTRAINTS ON A DEFORMATION MAP AND SYSTEM FOR IMPLEMENTING SAME

(75) Inventors: Weiguo Lu, Madison, WI (US);
Gustavo H. Olivera, Madison, WI (US);
Kenneth J. Ruchala, Madison, WI (US);
Eric Schnarr, McFarland, WI (US)

(73) Assignee: TomoTherapy Incorporated, Madison, WI (US)

( * ) Notice: Subject to any disclaimer, the term of this patent is extended or adjusted under 35 U.S.C. 154(b) by 39 days.

(21) Appl. No.: 11/459,061

(22) Filed: Jul. 21, 2006

(65) Prior Publication Data

US 2007/0189591 A1 Aug. 16, 2007

Related U.S. Application Data

(60) Provisional application No. 60/701,580, filed on Jul. 22, 2005.

(51) Int. Cl.
*G06K 9/00* (2006.01)
*G06K 9/64* (2006.01)
*G06K 9/32* (2006.01)
*A61B 5/05* (2006.01)

(52) U.S. Cl. .................. 382/128; 382/130; 382/131; 382/278; 382/294; 600/427

(58) Field of Classification Search .............. 382/128, 382/130, 131, 277, 278, 294; 600/427
See application file for complete search history.

(56) References Cited

U.S. PATENT DOCUMENTS

| | | | |
|---|---|---|---|
| 3,949,265 A | 4/1976 | Holl | |
| 3,964,467 A | 6/1976 | Rose | |
| 4,006,422 A | 2/1977 | Schriber | |
| 4,032,810 A | 6/1977 | Eastham et al. | |
| 4,149,081 A | 4/1979 | Seppi | |
| 4,181,894 A | 1/1980 | Pottier | |

(Continued)

FOREIGN PATENT DOCUMENTS

CA 2091275 9/1993

(Continued)

OTHER PUBLICATIONS

Rueckert et al. Nonrigid Registration Using Free-Form Deformations: Application to Breast MR Images. IEEE Transactions on Medical Imaging. Aug. 1999, vol. 18, No. 8, pp. 712-721.*

(Continued)

*Primary Examiner*—John B Strege
(74) *Attorney, Agent, or Firm*—Michael Best & Friedrich LLP

(57) ABSTRACT

A system and method of placing constraints on a deformation map. The method includes the acts of generating a deformation map between two images, identifying a defined structure in one of the images, applying the deformation map to relate the defined structure from the one image onto the other image to create a deformation-based defined structure, modifying the deformation-based defined structure, and updating the deformation map in response to the step of modifying the deformation-based defined structure.

30 Claims, 13 Drawing Sheets

U.S. PATENT DOCUMENTS

| | | |
|---|---|---|
| 4,189,470 A | 2/1980 | Rose |
| 4,208,185 A | 6/1980 | Sawai et al. |
| 4,273,867 A | 6/1981 | Lin et al. |
| 4,314,180 A | 2/1982 | Salisbury |
| 4,335,465 A | 6/1982 | Christiansen et al. |
| 4,388,560 A | 6/1983 | Robinson et al. |
| 4,393,334 A | 7/1983 | Glaser |
| 4,395,631 A | 7/1983 | Salisbury |
| 4,401,765 A | 8/1983 | Craig et al. |
| 4,426,582 A | 1/1984 | Orloff et al. |
| 4,446,403 A | 5/1984 | Cuomo et al. |
| 4,480,042 A | 10/1984 | Craig et al. |
| 4,570,103 A | 2/1986 | Schoen |
| 4,664,869 A | 5/1987 | Mirzadeh et al. |
| 4,703,018 A | 10/1987 | Craig et al. |
| 4,715,056 A | 12/1987 | Vlasbloem et al. |
| 4,736,106 A | 4/1988 | Kashy et al. |
| 4,752,692 A | 6/1988 | Jergenson et al. |
| 4,754,760 A | 7/1988 | Fukukita et al. |
| 4,815,446 A | 3/1989 | McIntosh |
| 4,818,914 A | 4/1989 | Brodie |
| 4,868,844 A | 9/1989 | Nunan |
| 4,870,287 A | 9/1989 | Cole et al. |
| 4,879,518 A | 11/1989 | Broadhurst |
| 4,912,731 A | 3/1990 | Nardi |
| 4,936,308 A | 6/1990 | Fukukita et al. |
| 4,987,309 A | 1/1991 | Klasen et al. |
| 4,998,268 A | 3/1991 | Winter |
| 5,003,998 A | 4/1991 | Collett |
| 5,008,907 A | 4/1991 | Norman et al. |
| 5,012,111 A | 4/1991 | Ueda |
| 5,065,315 A | 11/1991 | Garcia |
| 5,073,913 A | 12/1991 | Martin |
| 5,084,682 A | 1/1992 | Swenson et al. |
| 5,107,222 A | 4/1992 | Tsuzuki |
| 5,124,658 A | 6/1992 | Adler |
| 5,210,414 A | 5/1993 | Wallace et al. |
| 5,250,388 A | 10/1993 | Schoch, Jr. et al. |
| 5,317,616 A | 5/1994 | Swerdloff et al. |
| 5,335,255 A | 8/1994 | Seppi et al. |
| 5,346,548 A | 9/1994 | Mehta |
| 5,351,280 A | 9/1994 | Swerdloff et al. |
| 5,382,914 A | 1/1995 | Hamm et al. |
| 5,391,139 A | 2/1995 | Edmundson |
| 5,394,452 A | 2/1995 | Swerdloff et al. |
| 5,405,309 A | 4/1995 | Carden, Jr. |
| 5,442,675 A | 8/1995 | Swerdloff et al. |
| 5,453,310 A | 9/1995 | Andersen et al. |
| 5,466,587 A | 11/1995 | Fitzpatrick-McElligott et al. |
| 5,471,516 A | 11/1995 | Nunan |
| 5,483,122 A | 1/1996 | Derbenev et al. |
| 5,489,780 A | 2/1996 | Diamondis |
| 5,523,578 A | 6/1996 | Herskovic |
| 5,528,650 A | 6/1996 | Swerdloff et al. |
| 5,548,627 A | 8/1996 | Swerdloff et al. |
| 5,576,602 A | 11/1996 | Hiramoto et al. |
| 5,578,909 A | 11/1996 | Billen |
| 5,581,156 A | 12/1996 | Roberts et al. |
| 5,596,619 A | 1/1997 | Carol |
| 5,596,653 A | 1/1997 | Kurokawa |
| 5,621,779 A | 4/1997 | Hughes et al. |
| 5,622,187 A | 4/1997 | Carol |
| 5,625,663 A | 4/1997 | Swerdloff et al. |
| 5,627,041 A | 5/1997 | Shartle |
| 5,641,584 A | 6/1997 | Andersen et al. |
| 5,647,663 A | 7/1997 | Holmes |
| 5,651,043 A | 7/1997 | Tsuyuki et al. |
| 5,661,377 A | 8/1997 | Mishin et al. |
| 5,661,773 A | 8/1997 | Swerdloff et al. |
| 5,667,803 A | 9/1997 | Paronen et al. |
| 5,668,371 A | 9/1997 | Deasy et al. |
| 5,673,300 A | 9/1997 | Reckwerdt et al. |
| 5,692,507 A | 12/1997 | Seppi et al. |
| 5,695,443 A | 12/1997 | Brent et al. |
| 5,712,482 A | 1/1998 | Gaiser et al. |
| 5,721,123 A | 2/1998 | Hayes et al. |
| 5,724,400 A | 3/1998 | Swerdloff et al. |
| 5,729,028 A | 3/1998 | Rose |
| 5,734,168 A | 3/1998 | Yao |
| 5,747,254 A | 5/1998 | Pontius |
| 5,751,781 A | 5/1998 | Brown et al. |
| 5,753,308 A | 5/1998 | Andersen et al. |
| 5,754,622 A | 5/1998 | Hughes |
| 5,754,623 A | 5/1998 | Seki |
| 5,760,395 A | 6/1998 | Johnstone |
| 5,802,136 A | 9/1998 | Carol |
| 5,811,944 A | 9/1998 | Sampayan et al. |
| 5,815,547 A | 9/1998 | Shepherd et al. |
| 5,818,058 A | 10/1998 | Nakanishi et al. |
| 5,818,902 A | 10/1998 | Yu |
| 5,820,553 A | 10/1998 | Hughes |
| 5,821,051 A | 10/1998 | Androphy et al. |
| 5,821,705 A | 10/1998 | Caporaso et al. |
| 5,834,454 A | 11/1998 | Kitano et al. |
| 5,836,905 A | 11/1998 | Lemelson et al. |
| 5,842,175 A | 11/1998 | Andros et al. |
| 5,866,912 A | 2/1999 | Slater et al. |
| 5,870,447 A | 2/1999 | Powell et al. |
| 5,877,023 A | 3/1999 | Sautter et al. |
| 5,877,192 A | 3/1999 | Lindberg et al. |
| 5,912,134 A | 6/1999 | Shartle |
| 5,920,601 A | 7/1999 | Nigg et al. |
| 5,953,461 A | 9/1999 | Yamada |
| 5,962,995 A | 10/1999 | Avnery |
| 5,963,615 A | 10/1999 | Egley et al. |
| 5,969,367 A | 10/1999 | Hiramoto et al. |
| 5,977,100 A | 11/1999 | Kitano et al. |
| 5,983,424 A | 11/1999 | Naslund |
| 5,986,274 A | 11/1999 | Akiyama et al. |
| 6,011,825 A | 1/2000 | Welch et al. |
| 6,020,135 A | 2/2000 | Levine et al. |
| 6,020,538 A | 2/2000 | Han et al. |
| 6,029,079 A | 2/2000 | Cox et al. |
| 6,038,283 A | 3/2000 | Carol et al. |
| 6,049,587 A | 4/2000 | Leksell et al. |
| 6,066,927 A | 5/2000 | Koudijs |
| 6,069,459 A | 5/2000 | Koudijs |
| 6,071,748 A | 6/2000 | Modlin et al. |
| 6,094,760 A | 8/2000 | Nonaka et al. |
| 6,127,688 A | 10/2000 | Wu |
| 6,152,599 A | 11/2000 | Salter |
| 6,171,798 B1 | 1/2001 | Levine et al. |
| 6,178,345 B1 | 1/2001 | Vilsmeier et al. |
| 6,197,328 B1 | 3/2001 | Yanagawa |
| 6,198,957 B1 | 3/2001 | Green |
| 6,200,959 B1 | 3/2001 | Haynes et al. |
| 6,204,510 B1 | 3/2001 | Ohkawa |
| 6,207,400 B1 | 3/2001 | Kwon |
| 6,218,675 B1 | 4/2001 | Akiyama et al. |
| 6,222,905 B1 | 4/2001 | Yoda et al. |
| 6,241,670 B1 | 6/2001 | Nambu |
| 6,242,747 B1 | 6/2001 | Sugitani et al. |
| 6,264,825 B1 | 7/2001 | Blackburn et al. |
| 6,265,837 B1 | 7/2001 | Akiyama et al. |
| 6,279,579 B1 | 8/2001 | Riaziat et al. |
| 6,291,823 B1 | 9/2001 | Doyle et al. |
| 6,316,776 B1 | 11/2001 | Hiramoto et al. |
| 6,319,469 B1 | 11/2001 | Mian et al. |
| 6,322,249 B1 | 11/2001 | Wofford et al. |
| 6,331,194 B1 | 12/2001 | Elizondo-Decanini et al. |
| 6,345,114 B1 | 2/2002 | Mackie et al. |
| 6,360,116 B1 | 3/2002 | Jackson, Jr. et al. |
| 6,385,286 B1 | 5/2002 | Fitchard et al. |
| 6,385,288 B1 | 5/2002 | Kanematsu |

| Patent | Date | Inventor |
|---|---|---|
| 6,393,096 B1 | 5/2002 | Carol et al. |
| 6,405,072 B1 | 6/2002 | Cosman |
| 6,407,505 B1 | 6/2002 | Bertsche |
| 6,417,178 B1 | 7/2002 | Klunk et al. |
| 6,424,856 B1 | 7/2002 | Vilsmeier et al. |
| 6,428,547 B1 | 8/2002 | Vilsmeier et al. |
| 6,433,349 B2 | 8/2002 | Akayama et al. |
| 6,438,202 B1 | 8/2002 | Olivera et al. |
| 6,455,844 B1 | 9/2002 | Meyer |
| 6,462,490 B1 | 10/2002 | Matsuda et al. |
| 6,465,957 B1 | 10/2002 | Whitham et al. |
| 6,466,644 B1 | 10/2002 | Hughes et al. |
| 6,469,058 B1 | 10/2002 | Grove et al. |
| 6,472,834 B2 | 10/2002 | Hiramoto et al. |
| 6,473,490 B1 | 10/2002 | Siochi |
| 6,475,994 B2 | 11/2002 | Tomalia et al. |
| 6,482,604 B2 | 11/2002 | Kwon |
| 6,484,144 B2 | 11/2002 | Martin et al. |
| 6,487,274 B2 | 11/2002 | Bertsche |
| 6,493,424 B2 | 12/2002 | Whitham |
| 6,497,358 B1 | 12/2002 | Walsh |
| 6,498,011 B2 | 12/2002 | Hohn et al. |
| 6,500,343 B2 | 12/2002 | Siddiqi |
| 6,504,899 B2 | 1/2003 | Pugachev et al. |
| 6,510,199 B1 | 1/2003 | Hughes et al. |
| 6,512,942 B1 | 1/2003 | Burdette et al. |
| 6,516,046 B1 | 2/2003 | Frohlich et al. |
| 6,527,443 B1 | 3/2003 | Vilsmeier et al. |
| 6,531,449 B2 | 3/2003 | Khojasteh et al. |
| 6,535,837 B1 | 3/2003 | Schach Von Wittenau |
| 6,552,338 B1 | 4/2003 | Doyle |
| 6,558,961 B1 | 5/2003 | Sarphie et al. |
| 6,560,311 B1 | 5/2003 | Shepard et al. |
| 6,562,376 B2 | 5/2003 | Hooper et al. |
| 6,584,174 B2 | 6/2003 | Schubert et al. |
| 6,586,409 B1 | 7/2003 | Wheeler |
| 6,605,297 B2 | 8/2003 | Nadachi et al. |
| 6,611,700 B1 | 8/2003 | Vilsmeier et al. |
| 6,617,768 B1 | 9/2003 | Hansen |
| 6,618,467 B1 | 9/2003 | Ruchala et al. |
| 6,621,889 B1 | 9/2003 | Mostafavi |
| 6,633,686 B1 * | 10/2003 | Bakircioglu et al. ........ 382/294 |
| 6,634,790 B1 | 10/2003 | Salter, Jr. |
| 6,636,622 B2 | 10/2003 | Mackie et al. |
| 6,637,056 B1 | 10/2003 | Tybinkowski et al. |
| 6,646,383 B2 | 11/2003 | Bertsche et al. |
| 6,653,547 B2 | 11/2003 | Akamatsu |
| 6,661,870 B2 | 12/2003 | Kapatoes et al. |
| 6,688,187 B1 | 2/2004 | Masquelier |
| 6,690,965 B1 | 2/2004 | Riaziat et al. |
| 6,697,452 B2 | 2/2004 | Xing |
| 6,705,984 B1 | 3/2004 | Angha |
| 6,713,668 B2 | 3/2004 | Akamatsu |
| 6,713,976 B1 | 3/2004 | Zumoto et al. |
| 6,714,620 B2 | 3/2004 | Caflisch et al. |
| 6,714,629 B2 | 3/2004 | Vilsmeier |
| 6,716,162 B2 | 4/2004 | Hakamata |
| 6,723,334 B1 | 4/2004 | McGee et al. |
| 6,741,674 B2 | 5/2004 | Lee |
| 6,760,402 B2 | 7/2004 | Ghelmansarai |
| 6,774,383 B2 | 8/2004 | Norimine et al. |
| 6,787,771 B2 | 9/2004 | Bashkirov et al. |
| 6,787,983 B2 | 9/2004 | Yamanobe et al. |
| 6,788,764 B2 | 9/2004 | Saladin et al. |
| 6,792,073 B2 | 9/2004 | Deasy et al. |
| 6,796,164 B2 | 9/2004 | McLoughlin et al. |
| 6,800,866 B2 | 10/2004 | Amemiya et al. |
| 6,822,244 B2 | 11/2004 | Beloussov et al. |
| 6,822,247 B2 | 11/2004 | Sasaki |
| 6,838,676 B1 | 1/2005 | Jackson |
| 6,842,502 B2 | 1/2005 | Jaffray et al. |
| 6,844,689 B1 | 1/2005 | Brown et al. |
| 6,871,171 B1 | 3/2005 | Agur et al. |
| 6,873,115 B2 | 3/2005 | Sagawa et al. |
| 6,873,123 B2 | 3/2005 | Marchand et al. |
| 6,878,951 B2 | 4/2005 | Ma |
| 6,882,702 B2 | 4/2005 | Luo |
| 6,882,705 B2 | 4/2005 | Egley et al. |
| 6,888,326 B2 | 5/2005 | Amaldi et al. |
| 6,889,695 B2 | 5/2005 | Pankratov et al. |
| 6,907,282 B2 | 6/2005 | Siochi |
| 6,922,455 B2 | 7/2005 | Jurczyk et al. |
| 6,929,398 B1 | 8/2005 | Tybinkowski et al. |
| 6,936,832 B2 | 8/2005 | Norimine et al. |
| 6,955,464 B1 | 10/2005 | Tybinkowski et al. |
| 6,963,171 B2 | 11/2005 | Sagawa et al. |
| 6,974,254 B2 | 12/2005 | Paliwal et al. |
| 6,984,835 B2 | 1/2006 | Harada |
| 6,990,167 B2 | 1/2006 | Chen |
| 7,015,490 B2 | 3/2006 | Wang et al. |
| 7,046,762 B2 | 5/2006 | Lee |
| 7,051,605 B2 | 5/2006 | Lagraff et al. |
| 7,060,997 B2 | 6/2006 | Norimine et al. |
| 7,077,569 B1 | 7/2006 | Tybinkowski et al. |
| 7,081,619 B2 | 7/2006 | Bashkirov et al. |
| 7,084,410 B2 | 8/2006 | Beloussov et al. |
| 7,087,200 B2 | 8/2006 | Taboas et al. |
| 7,112,924 B2 | 9/2006 | Hanna |
| 7,130,372 B2 | 10/2006 | Kusch et al. |
| 7,154,991 B2 | 12/2006 | Earnst et al. |
| 7,186,986 B2 | 3/2007 | Hinderer et al. |
| 7,186,991 B2 | 3/2007 | Kato et al. |
| 7,203,272 B2 | 4/2007 | Chen |
| 7,209,547 B2 | 4/2007 | Baier et al. |
| 7,221,733 B1 | 5/2007 | Takai et al. |
| 7,252,307 B2 | 8/2007 | Kanbe et al. |
| 7,257,196 B2 | 8/2007 | Brown et al. |
| 7,391,026 B2 | 6/2008 | Trinkaus et al. |
| 2002/0007918 A1 | 1/2002 | Owen et al. |
| 2002/0077545 A1 | 6/2002 | Takahashi et al. |
| 2002/0080915 A1 | 6/2002 | Frohlich |
| 2002/0085668 A1 | 7/2002 | Blumhofer et al. |
| 2002/0091314 A1 | 7/2002 | Schlossbauer et al. |
| 2002/0115923 A1 | 8/2002 | Erbel |
| 2002/0120986 A1 | 9/2002 | Erbel et al. |
| 2002/0122530 A1 | 9/2002 | Erbel et al. |
| 2002/0136439 A1 | 9/2002 | Ruchala et al. |
| 2002/0150207 A1 | 10/2002 | Kapatoes et al. |
| 2002/0187502 A1 | 12/2002 | Waterman et al. |
| 2002/0193685 A1 | 12/2002 | Mate et al. |
| 2003/0007601 A1 | 1/2003 | Jaffray et al. |
| 2003/0031298 A1 | 2/2003 | Xing |
| 2003/0086527 A1 | 5/2003 | Speiser et al. |
| 2003/0105650 A1 | 6/2003 | Lombardo et al. |
| 2003/0174872 A1 | 9/2003 | Chalana et al. |
| 2004/0010418 A1 | 1/2004 | Buonocore et al. |
| 2004/0068182 A1 | 4/2004 | Misra |
| 2004/0116804 A1 | 6/2004 | Mostafavi |
| 2004/0165696 A1 | 8/2004 | Lee |
| 2004/0202280 A1 | 10/2004 | Besson |
| 2004/0230115 A1 | 11/2004 | Scarantino et al. |
| 2004/0254492 A1 | 12/2004 | Zhang et al. |
| 2004/0254773 A1 | 12/2004 | Zhang et al. |
| 2004/0264640 A1 | 12/2004 | Myles |
| 2005/0013406 A1 | 1/2005 | Dyk et al. |
| 2005/0031181 A1 | 2/2005 | Bi et al. |
| 2005/0080332 A1 | 4/2005 | Shiu et al. |
| 2005/0096515 A1 | 5/2005 | Geng |
| 2005/0123092 A1 | 6/2005 | Mistretta et al. |
| 2005/0143965 A1 | 6/2005 | Failla et al. |
| 2005/0180544 A1 * | 8/2005 | Sauer et al. ................. 378/195 |
| 2005/0197564 A1 | 9/2005 | Dempsey |
| 2005/0251029 A1 * | 11/2005 | Khamene et al. ............ 600/427 |
| 2006/0074292 A1 | 4/2006 | Thomson et al. |
| 2006/0083349 A1 | 4/2006 | Harari et al. |
| 2006/0100738 A1 | 5/2006 | Alsafadi et al. |

| | | |
|---|---|---|
| 2006/0133568 A1 | 6/2006 | Moore |
| 2006/0193429 A1 | 8/2006 | Chen |
| 2006/0193441 A1 | 8/2006 | Cadman |
| 2006/0285639 A1 | 12/2006 | Olivera et al. |
| 2007/0041494 A1 | 2/2007 | Ruchala et al. |
| 2007/0041495 A1 | 2/2007 | Olivera et al. |
| 2007/0041497 A1 | 2/2007 | Schnarr et al. |
| 2007/0041498 A1 | 2/2007 | Olivera et al. |
| 2007/0041499 A1 | 2/2007 | Lu et al. |
| 2007/0041500 A1 | 2/2007 | Olivera et al. |
| 2007/0043286 A1 | 2/2007 | Lu et al. |
| 2007/0076846 A1 | 4/2007 | Ruchala et al. |
| 2007/0088573 A1 | 4/2007 | Ruchala et al. |
| 2007/0104316 A1 | 5/2007 | Ruchala et al. |
| 2007/0127623 A1 | 6/2007 | Goldman et al. |
| 2007/0189591 A1 | 8/2007 | Lu et al. |
| 2007/0195922 A1 | 8/2007 | Mackie et al. |
| 2007/0195929 A1 | 8/2007 | Ruchala et al. |
| 2007/0195930 A1 | 8/2007 | Kapatoes et al. |
| 2007/0201613 A1 | 8/2007 | Lu et al. |
| 2007/0211857 A1 | 9/2007 | Urano et al. |

FOREIGN PATENT DOCUMENTS

| | | |
|---|---|---|
| CA | 2180227 | 12/1996 |
| WO | 03/076003 | 9/2003 |
| WO | 2004057515 | 7/2004 |

OTHER PUBLICATIONS

Young et al. Registration-Based Morphing of Active Contours for Segmentation of CT Scans. Mathematical Biosciences and Engineering. Jan. 2005, vol. 2, No. 1. pp. 79-96.*

Yezzi et al. A Variational Framework for Joint Segmentation and Registration. Mathematical Methods in Biomedical Image Analysis, 2001, pp. 1-8.*

PCT/US06/28536 International Search Report and Written Opinion mailed Dec. 10, 2007.

Ronald D. Rogus et al., "Accuracy of a Photogrammetry-Based Patient Positioning and Monitoring System for Radiation Therapy," Medical Physics, vol. 26, Issue 5, May 1999.

Ruchala, Kenneth, et al, "Adaptive IMRT with Tomotherapy", RT Image, vol. 14, No. 25, pp. 14-18, Jun. 18, 2001.

Marcelo Bertalmio, et al., "Morphing Active Contours", IEEE Transactions on Pattern Analysis and Machine Intelligence, vol. 22, No. 7, pp. 733-737, Jul. 2000.

Lu, W., et al., Automatic Re-Contouring in 4D Radiotherapy:, Physical Medical Biology, 2006, Mar. 7, 51(5): 1077-99.

Lu, W., et al., 2004 Automatic Re-Contouring for 4-D Planning and Adaptive Radiotherapy, The 90th RSNA Meeting, Chicago, Illinois, (abstract: Radiology 227 (p) 543).

Lu, W., et al., 2004 Automatic Re-Contouring Regions of Interest Based on Deformable Registration and Surface Reconstruction, AAPM 2004, (abstract: Medical Physics 31, 1845-6).

* cited by examiner

METHOD OF PLACING CONSTRAINTS ON A DEFORMATION MAP AND SYSTEM FOR IMPLEMENTING SAME

RELATED APPLICATIONS

This application claims priority to U.S. Provisional Patent Application No. 60/701,580, filed on Jul. 22, 2005, titled SYSTEM AND METHOD FOR FEEDBACK GUIDED QUALITY ASSURANCE AND ADAPTATIONS TO RADIATION THERAPY TREATMENT, the entire contents of which are incorporated herein by reference.

BACKGROUND

Over the past decades improvements in computers and networking, radiation therapy treatment planning software, and medical imaging modalities (CT, MRI, US, and PET) have been incorporated into radiation therapy practice. These improvements have led to the development of image guided radiation therapy ("IGRT"). IGRT is radiation therapy that uses cross-sectional images of the patient's internal anatomy to better target the radiation dose in the tumor while reducing the radiation exposure to healthy organs. The radiation dose delivered to the tumor is controlled with intensity modulated radiation therapy ("IMRT"), which involves changing the size, shape, and intensity of the radiation beam to conform to the size, shape, and location of the patient's tumor. IGRT and IMRT lead to improved control of the tumor while simultaneously reducing the potential for acute side effects due to irradiation of healthy tissue surrounding the tumor.

IMRT is becoming the standard of care in several countries. However, in many situations, IMRT is not used to treat a patient due to time, resources, and billing constraints. Daily images of the patient can be used to guarantee that the high gradients generated by IMRT plans are located on the correct position for patient treatment. Also these images can provide necessary information to adapt the plan online or offline if needed.

It is commonly known in the field of radiation therapy that there are many sources of uncertainty and change that can occur during a course of a patient's treatment. Some of these sources represent random errors, such as small differences in a patient's setup position each day. Other sources are attributable to physiological changes, which might occur if a patient's tumor regresses or the patient loses weight during therapy. A third possible category regards motion. Motion can potentially overlap with either of the other categories, as some motion might be more random and unpredictable, such as a patient coughing or passing gas, whereas other motion can be more regular, such as breathing motion, sometimes.

SUMMARY

In radiation therapy, uncertainties can affect the quality of a patient's treatment. For example, when delivering a treatment dose to a target region, it is standard practice to also treat a high-dose "margin" region about the target. This helps ensure that the target receives the desired dose, even if its location changes during the course of the treatment, or even during a single fraction. The less definite a target's location, the larger the margins that typically need to be used.

Adaptive radiation therapy generally refers to the concept of using feedback during the course of radiation therapy treatment to improve future treatments. Feedback can be used in off-line adaptive therapy processes and on-line adaptive therapy processes. Off-line adaptive therapy processes occur while the patient is not being treated, such as in between treatment fractions. In one version of this, during each fraction, a new CT image of the patient is acquired before or after each of the fractions. After the images are acquired from the first few treatment fractions, the images are evaluated to determine an effective envelope of the multi-day locations of target structures. A new plan can then be developed to better reflect the range of motion of the target structure, rather than using canonical assumptions of motion. A more complex version of off-line adaptive therapy is to recalculate the delivered dose after each fraction and accumulate these doses, potentially utilizing deformation techniques, during this accumulation to account for internal motion. The accumulated dose can then be compared to the planned dose, and if any discrepancies are noted, subsequent fractions can be modified to account for the changes.

On-line adaptive therapy processes typically occur while the patient is in the treatment room, and potentially, but not necessarily, during a treatment delivery. For example, some radiation therapy treatment systems are equipped with imaging systems, such as on-line CT or x-ray systems. These systems can be used prior to treatment to validate or adjust the patient's setup for the treatment delivery. The imaging systems may also be used to adapt the treatment during the actual treatment delivery. For example, an imaging system potentially can be used concurrently with treatment to modify the treatment delivery to reflect changes in patient anatomy.

One aspect of the present invention is to disclose new opportunities for the application of adaptive therapy techniques, and additional aspects are to present novel methods for adaptive therapy. In particular, adaptive therapy has typically focused on feedback to modify a patient's treatment, but the present invention focuses on adaptive therapy processes being used in a quality assurance context. This is particularly true in the context of whole-system verification.

For example, a detector can be used to collect information indicating how much treatment beam has passed through the patient, from which the magnitude of the treatment output can be determined as well as any radiation pattern that was used for the delivery. The benefit of this delivery verification process is that it enables the operator to detect errors in the machine delivery, such as an incorrect leaf pattern or machine output.

However, validating that the machine is functioning properly does not itself ensure proper delivery of a treatment plan, as one also needs to validate that the external inputs used to program the machine are effective and consistent. Thus, one aspect of the invention includes the broader concept of an adaptive-type feedback loop for improved quality assurance of the entire treatment process. In this aspect, the invention includes the steps of positioning the patient for treatment and using a method for image-guidance to determine the patient's position, repositioning the patient as necessary for treatment based upon the image-guidance, and beginning treatment. Then, either during or after treatment, recalculating the patient dose and incorporating the patient image information that had been collected before or during treatment. After completion of these steps, quality assurance data is collected to analyze the extent to which the delivery was not only performed as planned, but to validate that the planned delivery is reasonable in the context of the newly available data. In this regard, the concept of feedback is no longer being used to indicate changes to the treatment based on changes in the patient or delivery, but to validate the original delivery itself.

As an example, it is possible that a treatment plan might be developed for a patient, but that the image used for planning became corrupted, such as by applying an incorrect density calibration. In this case, the treatment plan will be based upon incorrect information, and might not deliver the correct dose to the patient. Yet, many quality assurance techniques will not detect this error because they will verify that the machine is operating as instructed, rather than checking whether the instructions to the machine are based on correct input information. Likewise, some adaptive therapy techniques could be applied to this delivery, but if the calibration problem of this example persisted, then the adapted treatments would suffer from similar flaws.

There are a number of processes that can be used to expand the use of feedback for quality assurance purposes. For example, in one embodiment, this process would include the delivery verification techniques described above. The validation of machine performance that these methods provide is a valuable component of a total-system quality assurance toolset. Moreover, the delivery verification processes can be expanded to analyze other system errors, such as deliveries based on images with a truncated field-of-view.

This method of quality assurance also benefits from the use of registration, and in particular, deformable registration, techniques. Registration is a method for determining the correlation between locations of a patient's anatomy or physiology across multiple images, and deformable registration is a method of doing this to account for non-rigid changes in anatomy between the images, phases, or times. As mentioned before, an important step in this method of quality assurance is the recalculation of dose based upon on-line images and feedback from the machine. When analyzing these doses, it is useful to accumulate the dose across multiple treatments to determine if any errors are being exacerbated or if they are mitigating each other.

It should be noted that while the invention presented is not fundamentally tied to adaptive therapy, in that these quality assurance processes can be applied without an adaptive therapy process in place, or adaptive therapy can be performed without these QA methods, there can be added benefits to using adaptive therapy in addition to these techniques. Therefore, if discrepancies are noted by using delivery feedback, these discrepancies can be rectified by any number of mechanisms either on-line or between fractions. The discrepancies to be remedied can extend beyond problems identified with the machine itself, for example, to inconsistencies with the process, or flawed inputs that are used to program the machine for a given treatment plan.

In one embodiment, the invention provides a method of placing constraints on a deformation map. The method comprises the acts of generating a deformation map between two images, identifying a defined structure in one of the images, applying the deformation map to relate the defined structure from the one image onto the other image to create a deformation-based defined structure, modifying the deformation-based defined structure, and updating the deformation map in response to the step of modifying the deformation-based defined structure.

In another embodiment, the invention provides a method of placing constraints on a deformation map. The method comprises the acts of generating a deformation map between two images, identifying a defined structure in one of the images, applying the deformation map to relate the defined structure from the one image onto the other image to create a deformation-based defined structure, modifying the deformation-based defined structure, updating the deformation map in response to the step of modifying the deformation-based defined structure, and generating a contour based on the updated deformation map.

In another embodiment, the invention provides a method of placing constraints on a deformation map. The method comprises the acts of a method of placing constraints on a deformation map. The method comprises the acts of generating a first contour set, generating a second contour set, and generating a deformation map between the first contour set and the second contour set.

Other aspects of the invention will become apparent by consideration of the detailed description and accompanying drawings.

DETAILED DESCRIPTION

Figure 1:
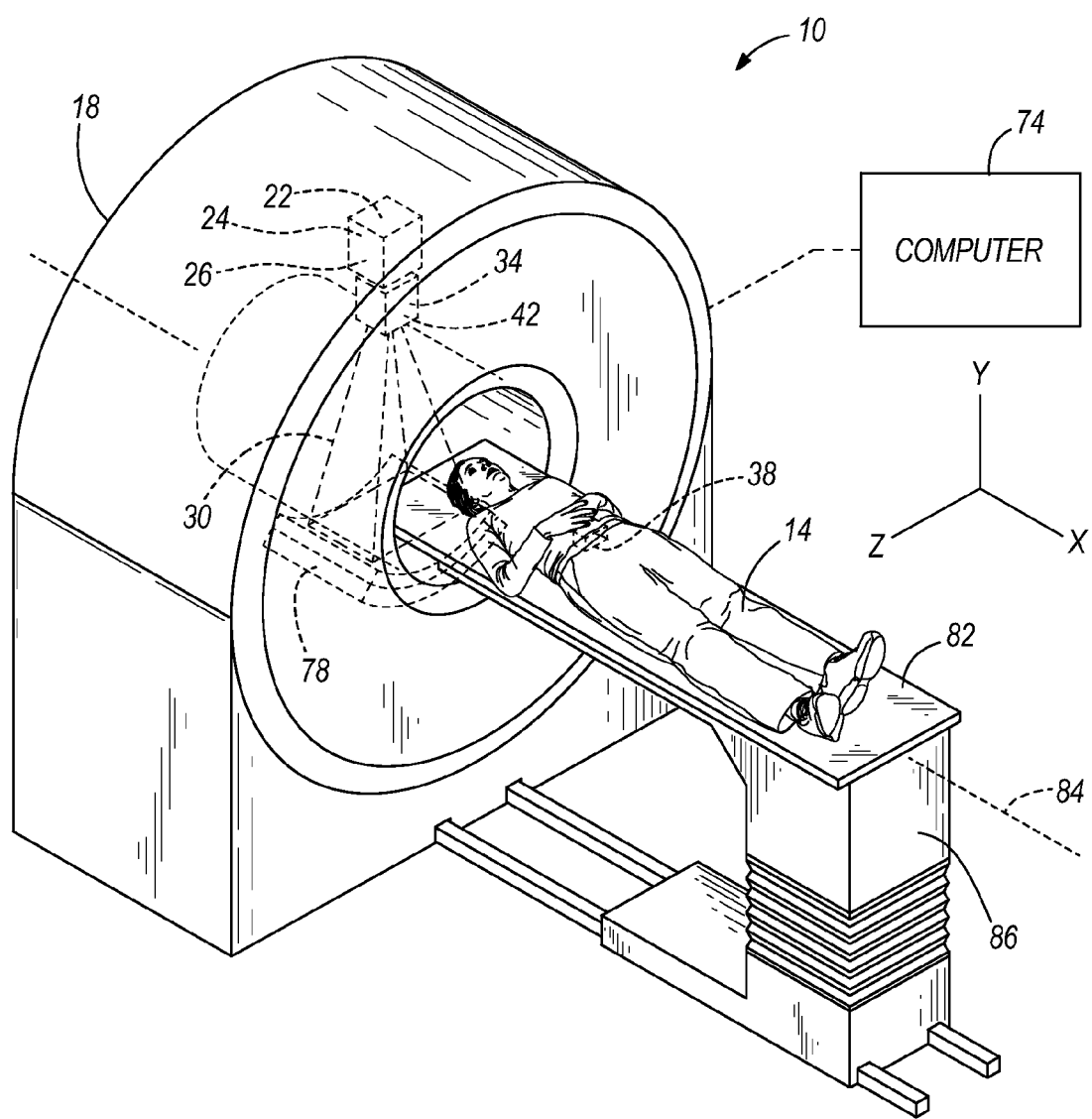
FIG. 1 is a perspective view of a radiation therapy treatment system embodying the invention.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

Although directional references, such as upper, lower, downward, upward, rearward, bottom, front, rear, etc., may be made herein in describing the drawings, these references are made relative to the drawings (as normally viewed) for convenience. These directions are not intended to be taken literally or limit the present invention in any form. In addition, terms such as "first", "second", and "third" are used herein for purposes of description and are not intended to indicate or imply relative importance or significance.

In addition, it should be understood that embodiments of the invention include both hardware, software, and electronic components or modules that, for purposes of discussion, may be illustrated and described as if the majority of the components were implemented solely in hardware. However, one of ordinary skill in the art, and based on a reading of this detailed description, would recognize that, in at least one embodiment, the electronic based aspects of the invention may be implemented in software. As such, it should be noted that a plurality of hardware and software based devices, as well as a plurality of different structural components may be utilized to implement the invention. Furthermore, and as described in subsequent paragraphs, the specific mechanical configurations illustrated in the drawings are intended to exemplify embodiments of the invention and that other alternative mechanical configurations are possible.

FIG. 1 illustrates a radiation therapy treatment system 10 that can provide radiation therapy to a patient 14. The radiation therapy treatment can include photon-based radiation therapy, brachytherapy, electron beam therapy, proton, neutron, or particle therapy, or other types of treatment therapy. The radiation therapy treatment system 10 includes a gantry 18. The gantry 18 can support a radiation module 22, which can include a radiation source 24 and a linear accelerator 26 operable to generate a beam 30 of radiation. Though the gantry 18 shown in the drawings is a ring gantry, i.e., it extends through a full 360° arc to create a complete ring or circle, other types of mounting arrangements may also be employed. For example, a C-type, partial ring gantry, or robotic arm could be used. Any other framework capable of positioning the radiation module 22 at various rotational and/or axial positions relative to the patient 14 may also be employed. In addition, the radiation source 24 may travel in path that does not follow the shape of the gantry 18. For example, the radiation source 24 may travel in a non-circular path even though the illustrated gantry 18 is generally circular-shaped.

The radiation module 22 can also include a modulation device 34 operable to modify or modulate the radiation beam 30. The modulation device 34 provides the modulation of the radiation beam 30 and directs the radiation beam 30 toward the patient 14. Specifically, the radiation beam 34 is directed toward a portion of the patient. Broadly speaking, the portion may include the entire body, but is generally smaller than the entire body and can be defined by a two-dimensional area and/or a three-dimensional volume. A portion desired to receive the radiation, which may be referred to as a target 38 or target region, is an example of a region of interest. Another type of region of interest is a region at risk. If a portion includes a region at risk, the radiation beam is preferably diverted from the region at risk. The patient 14 may have more than one target region that needs to receive radiation therapy. Such modulation is sometimes referred to as intensity modulated radiation therapy ("IMRT").

Figure 2:
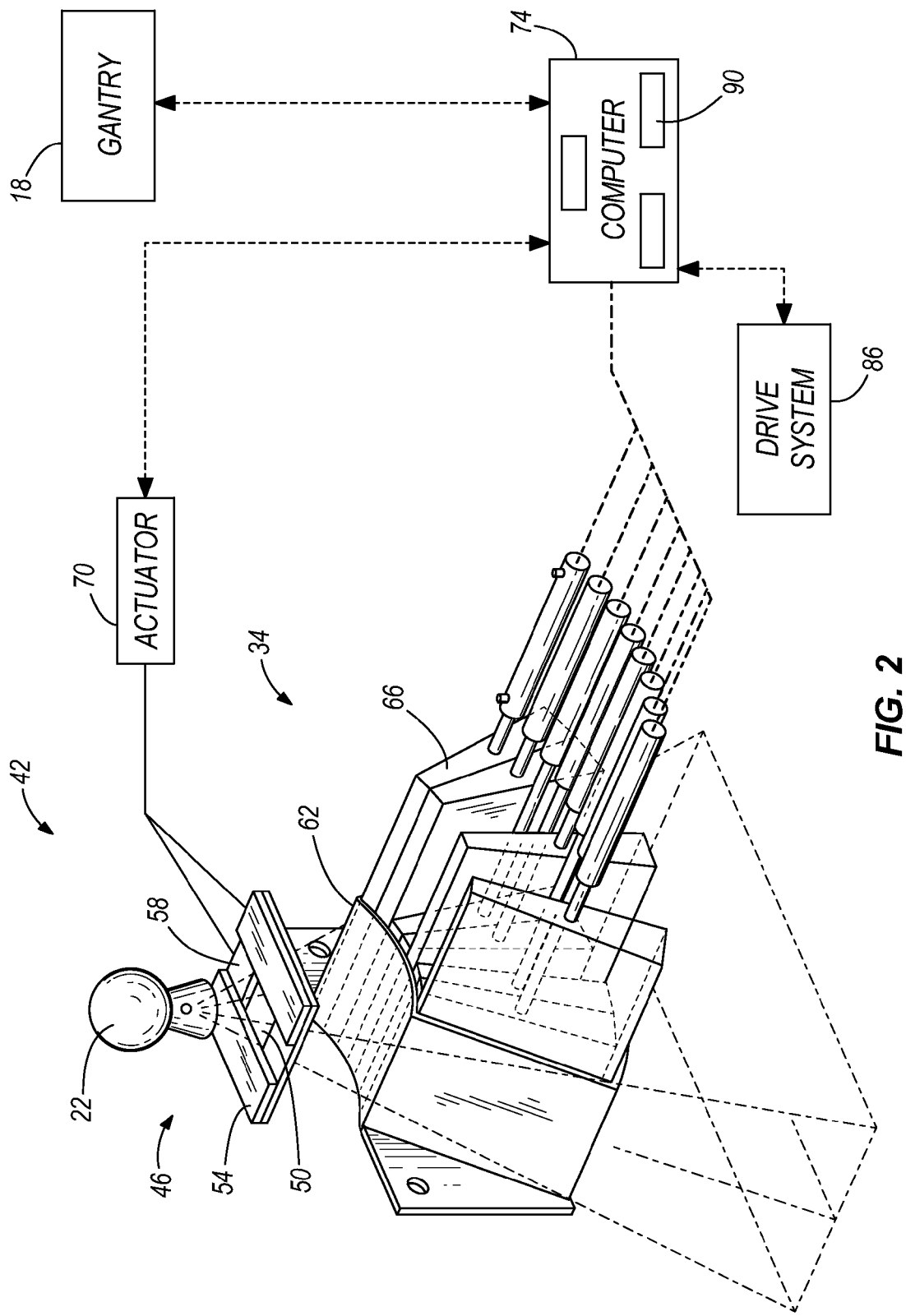
FIG. 2 is a perspective view of a multi-leaf collimator that can be used in the radiation therapy treatment system illustrated in FIG. 1.

The modulation device 34 can include a collimation device 42 as illustrated in FIG. 2. The collimation device 42 includes a set of jaws 46 that define and adjust the size of an aperture 50 through which the radiation beam 30 may pass. The jaws 46 include an upper jaw 54 and a lower jaw 58. The upper jaw 54 and the lower jaw 58 are moveable to adjust the size of the aperture 50.

In one embodiment, and illustrated in FIG. 2, the modulation device 34 can comprise a multi-leaf collimator 62, which includes a plurality of interlaced leaves 66 operable to move from position to position, to provide intensity modulation. It is also noted that the leaves 66 can be moved to a position anywhere between a minimally and maximally-open position. The plurality of interlaced leaves 66 modulate the strength, size, and shape of the radiation beam 30 before the radiation beam 30 reaches the target 38 on the patient 14. Each of the leaves 66 is independently controlled by an actuator 70, such as a motor or an air valve so that the leaf 66 can open and close quickly to permit or block the passage of radiation. The actuators 70 can be controlled by a computer 74 and/or controller.

The radiation therapy treatment system 10 can also include a detector 78, e.g., a kilovoltage or a megavoltage detector, operable to receive the radiation beam 30. The linear accelerator 26 and the detector 78 can also operate as a computed tomography (CT) system to generate CT images of the patient 14. The linear accelerator 26 emits the radiation beam 30 toward the target 38 in the patient 14. The target 38 absorbs some of the radiation. The detector 78 detects or measures the amount of radiation absorbed by the target 38. The detector 78 collects the absorption data from different angles as the linear accelerator 26 rotates around and emits radiation toward the patient 14. The collected absorption data is transmitted to the computer 74 to process the absorption data and to generate images of the patient's body tissues and organs. The images can also illustrate bone, soft tissues, and blood vessels.

The CT images can be acquired with a radiation beam 30 that has a fan-shaped geometry, a multi-slice geometry or a cone-beam geometry. In addition, the CT images can be acquired with the linear accelerator 26 delivering megavoltage energies or kilovoltage energies. It is also noted that the acquired CT images can be registered with previously acquired CT images (from the radiation therapy treatment system 10 or other image acquisition devices, such as other CT scanners, MRI systems, and PET systems). For example, the previously acquired CT images for the patient 14 can include identified targets 38 made through a contouring process. The newly acquired CT images for the patient 14 can be registered with the previously acquired CT images to assist in identifying the targets 38 in the new CT images. The registration process can use rigid or deformable registration tools.

In some embodiments, the radiation therapy treatment system 10 can include an x-ray source and a CT image detector. The x-ray source and the CT image detector operate in a similar manner as the linear accelerator 26 and the detector 78 as described above to acquire image data. The image data is transmitted to the computer 74 where it is processed to generate images of the patient's body tissues and organs.

The radiation therapy treatment system 10 can also include a patient support, such as a couch 82 (illustrated in FIG. 1), which supports the patient 14. The couch 82 moves along at least one axis 84 in the x, y, or z directions. In other embodiments of the invention, the patient support can be a device that is adapted to support any portion of the patient's body. The patient support is not limited to having to support the entire patient's body. The system 10 also can include a drive system 86 operable to manipulate the position of the couch 82. The drive system 86 can be controlled by the computer 74.

Figure 3:
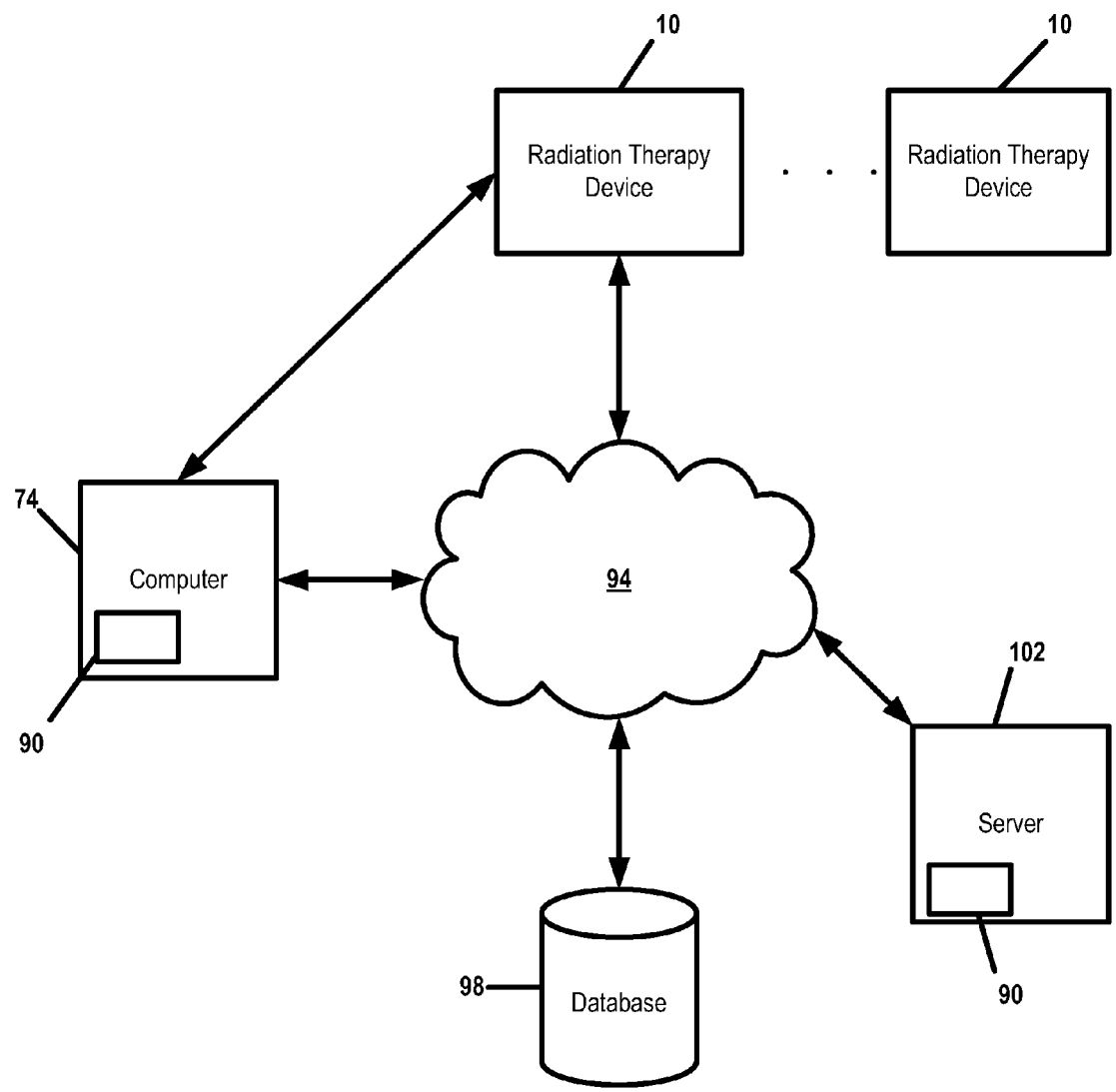
FIG. 3 is a schematic illustration of the radiation therapy treatment system of FIG. 1.

The computer 74, illustrated in FIGS. 2 and 3, includes an operating system for running various software programs and/or a communications application. In particular, the computer 74 can include a software program(s) 90 that operates to communicate with the radiation therapy treatment system 10. The software program(s) 90 is operable to receive data from external software programs and hardware and it is noted that data may be input to the software program(s) 90.

The computer 74 can include any suitable input/output device adapted to be accessed by medical personnel. The computer 74 can include typical hardware such as a processor, I/O interfaces, and storage devices or memory. The computer 74 can also include input devices such as a keyboard and a mouse. The computer 74 can further include standard output devices, such as a monitor. In addition, the computer 74 can include peripherals, such as a printer and a scanner.

The computer 74 can be networked with other computers 74 and radiation therapy treatment systems 10. The other computers 74 may include additional and/or different computer programs and software and are not required to be identical to the computer 74, described herein. The computers 74 and radiation therapy treatment system 10 can communicate with a network 94. The computers 74 and radiation therapy treatment systems 10 can also communicate with a database (s) 98 and a server(s) 102. It is noted that the software program(s) 90 could also reside on the server(s) 102.

The network 94 can be built according to any networking technology or topology or combinations of technologies and topologies and can include multiple sub-networks. Connections between the computers and systems shown in FIG. 3 can be made through local area networks ("LANs"), wide area networks ("WANs"), public switched telephone networks ("PSTNs"), wireless networks, Intranets, the Internet, or any other suitable networks. In a hospital or medical care facility, communication between the computers and systems shown in FIG. 3 can be made through the Health Level Seven ("HL7") protocol or other protocols with any version and/or other required protocol. HL7 is a standard protocol which specifies the implementation of interfaces between two computer applications (sender and receiver) from different vendors for electronic data exchange in health care environments. HL7 can allow health care institutions to exchange key sets of data from different application systems. Specifically, HL7 can define the data to be exchanged, the timing of the interchange, and the communication of errors to the application. The formats are generally generic in nature and can be configured to meet the needs of the applications involved.

Communication between the computers and systems shown in FIG. 3 can also occur through the Digital Imaging and Communications in Medicine ("DICOM") protocol with any version and/or other required protocol. DICOM is an international communications standard developed by NEMA that defines the format used to transfer medical image-related data between different pieces of medical equipment. DICOM RT refers to the standards that are specific to radiation therapy data.

The two-way arrows in FIG. 3 generally represent two-way communication and information transfer between the network 94 and any one of the computers 74 and the systems 10 shown in FIG. 3. However, for some medical and computerized equipment, only one-way communication and information transfer may be necessary.

Figure 4:
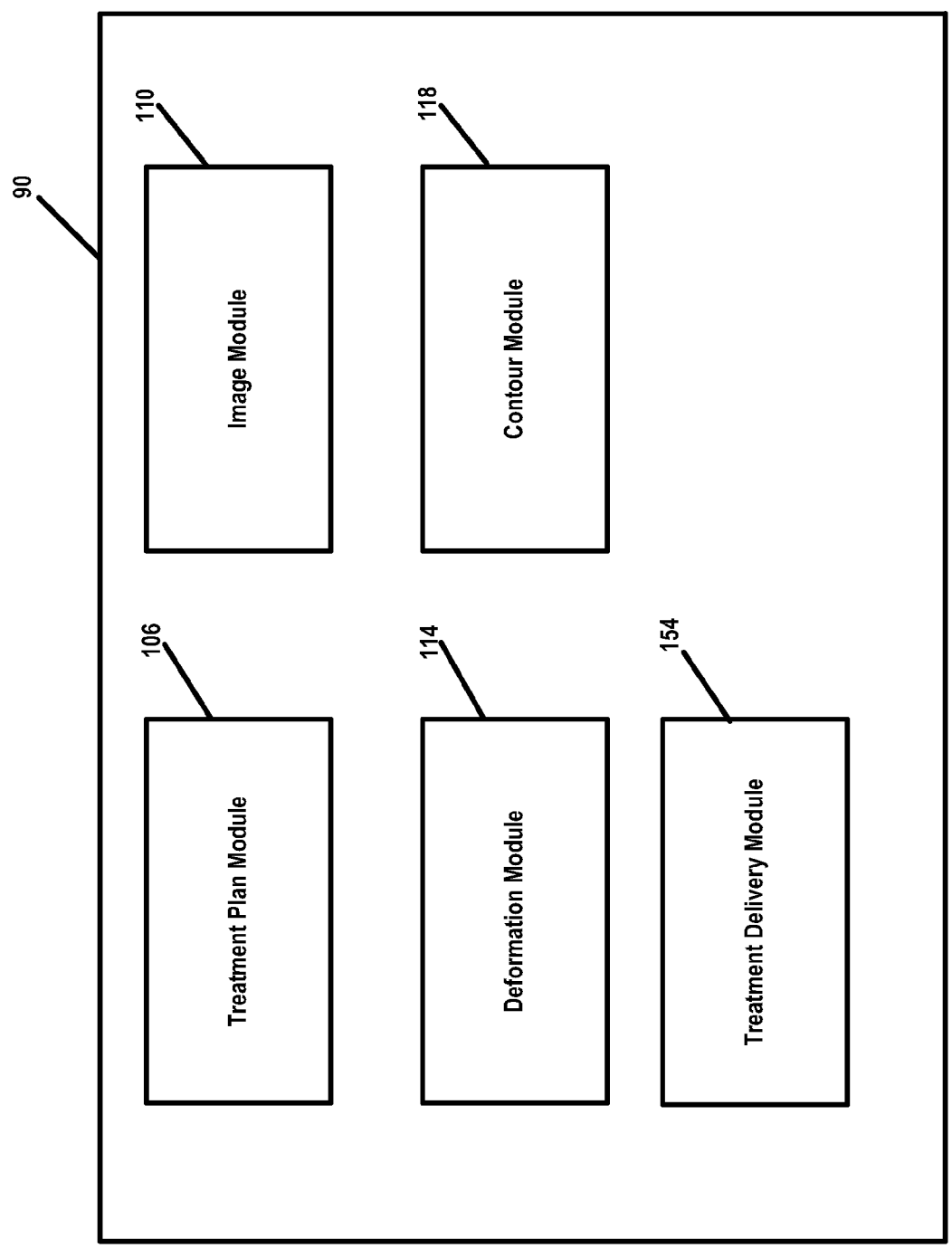
FIG. 4 is a schematic diagram of a software program used in the radiation therapy treatment system of a method of placing constraints on a deformation map according to one embodiment of the present invention.

The software program 90 includes a plurality of modules illustrated in FIG. 4 that communicate with one another to perform functions of the radiation therapy treatment process. The various modules communicate with one another to generate a deformation map of two images and to modify the deformation map in response to various modifications of one of the images. Generally, the deformation process occurs prior to commencing treatment delivery. It is noted that not all of the modules discussed below are needed to communicate and to carry out the various functions mentioned above.

The software program 90 includes a treatment plan module 106 operable to generate a treatment plan for the patient 14 based on data input to the system 10 by medical personnel. The data includes one or more images (e.g., planning images and/or pre-treatment images) of at least a portion of the patient 14. The treatment plan module 106 separates the treatment into a plurality of fractions and determines the radiation dose for each fraction or treatment based on the prescription input by medical personnel. The treatment plan module 106 also determines the radiation dose for the target 38 based on various contours drawn around the target 38. Multiple targets 38 may be present and included in the same treatment plan.

The software program 90 also includes an image module 110 operable to acquire images of at least a portion of the patient 14. Prior to delivery of the treatment plan, the image module 110 can instruct the on-board image device, such as a CT imaging device to acquire one or more pre-treatment images of the patient 14 before treatment commences. Other off-line imaging devices or systems may be used to acquire pre-treatment images of the patient 14, such as non-quantitative CT, MRI, PET, SPECT, ultrasound, transmission imaging, fluoroscopy, RF-based localization, and the like. The acquired pre-treatment image(s) can be used for registration of the patient 14 and/or to generate a deformation map to identify the differences between one or more of the planning images and one or more of the pre-treatment images.

The software program 90 also can include a deformation module 114 operable to receive data, such as image data from the image module 110 and the treatment planning module 106 and other patient and system data from the treatment plan module 106 to generate a deformation map of the images. The deformation module 114 can use deformation techniques to determine an accumulation of radiation dose for all of the delivered treatments.

A deformation map can be utilized to relate a plurality of images for dose calculation purposes. For example, a deformation map can relate a planning image that is useful for dose calculation, and an on-line image, which has qualitative value but less direct utility for dose calculation. This relationship can then be used to "remap" the more quantitative image to the qualitative shape of the on-line or less quantitative image. The resulting remapped image would be more appropriate than either of the planning image or the on-line image for dose calculation or quantitative applications as it would have the quantitative benefits of the first image, but with the updated anatomical information as contained in the second image. This is useful in a variety of cases, such as where the first image (e.g., a planning image) is a CT image and where the second image lacks quantitative image values (e.g., MRI, PET, SPECT, ultrasound, or non-quantitative CT, etc. images). A deformation map also can relate a reference image, such as a 3D image (e.g., a planning image or a pre-treatment image), and a time-based series of images, such as a 4D CT image to determine an amount of radiation dose delivered to the patient 14.

The deformation module 114 can correct for geometrical distortion, imperfections, and/or incompleteness in lieu of, or in addition to, quantitative limitations. For example, a current MRI image that represents anatomy well but includes geometric distortion might be remapped to a CT image that is not distorted. Or, multiple images can be used to simultaneously correct for distortion while representing anatomical changes.

The deformation map can be used to calculate radiation dose on patient images acquired after the planning image. It is also useful to accumulate the doses for multiple delivered fractions. The doses can be added based upon the location of the doses in physical space, but another method is to incorporate deformation methods into the process so as to add doses based upon the structures that received the dose, even if the structures have changed location. The deformation module 114 can calculate the doses of radiation that the patient 14 has received from previously delivered fractions.

A deformation map can be generated for purposes of defining a contour around a target 38. The software program 90 can include a contour module 118 operable to generate one or more contours on an image. Generally, medical personnel manually define a contour around a target 38 on a planning image. This process is time consuming. Newly acquired images (e.g., pre-treatment images) do not have the defined contour(s). It is desirable to generate contours on the new image based upon an old image that includes the contour(s). A deformation map can be used to assist in the contouring process by transferring the contour(s) from an old image onto a new image and can create time savings for the medical personnel while providing quality assurance measures.

Figure 5:
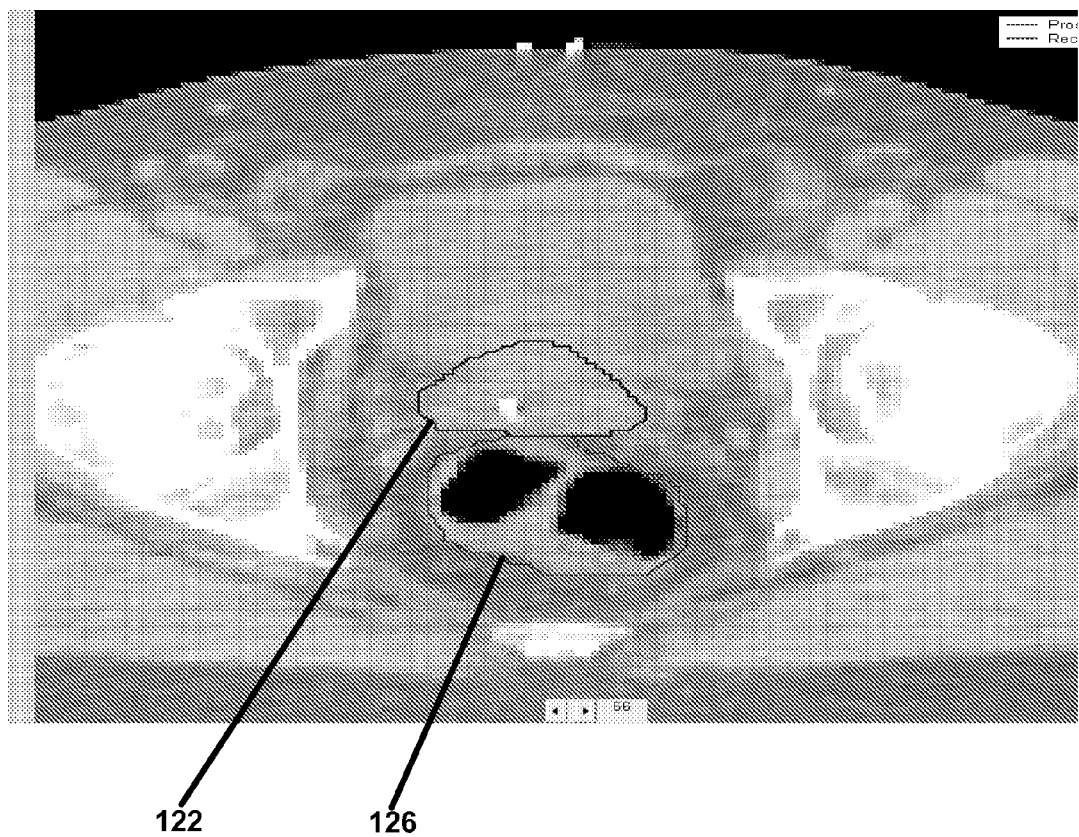
FIG. 5 is a planning image of a patient including contours.
Figure 6:
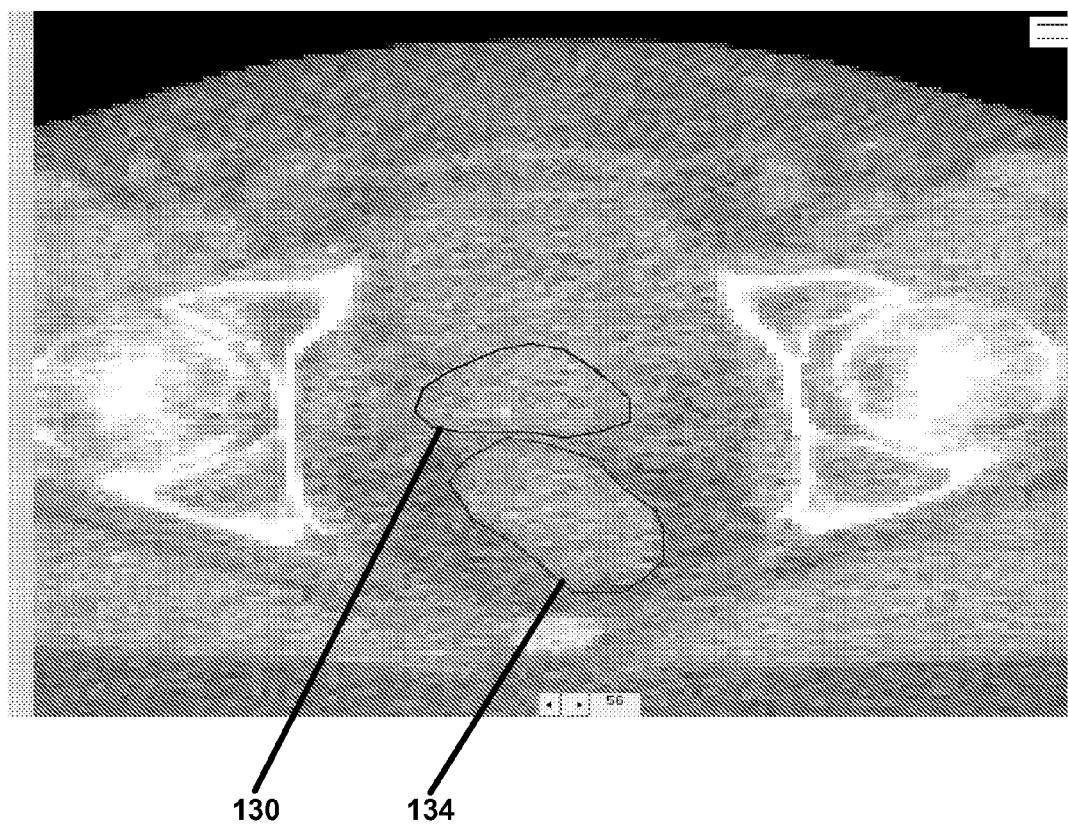
FIG. 6 is a pre-treatment image of a patient including manually-drawn contours.
Figure 7:
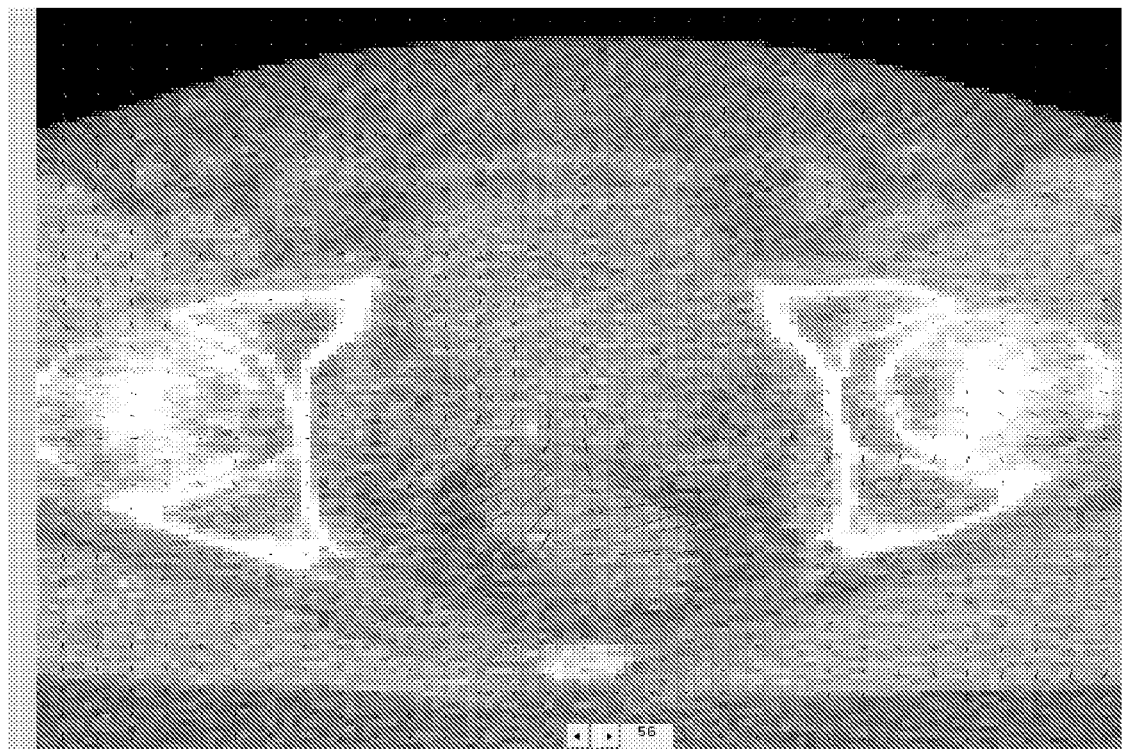
FIG. 7 is a deformation map between the images in FIGS. 5-6.
Figure 8:
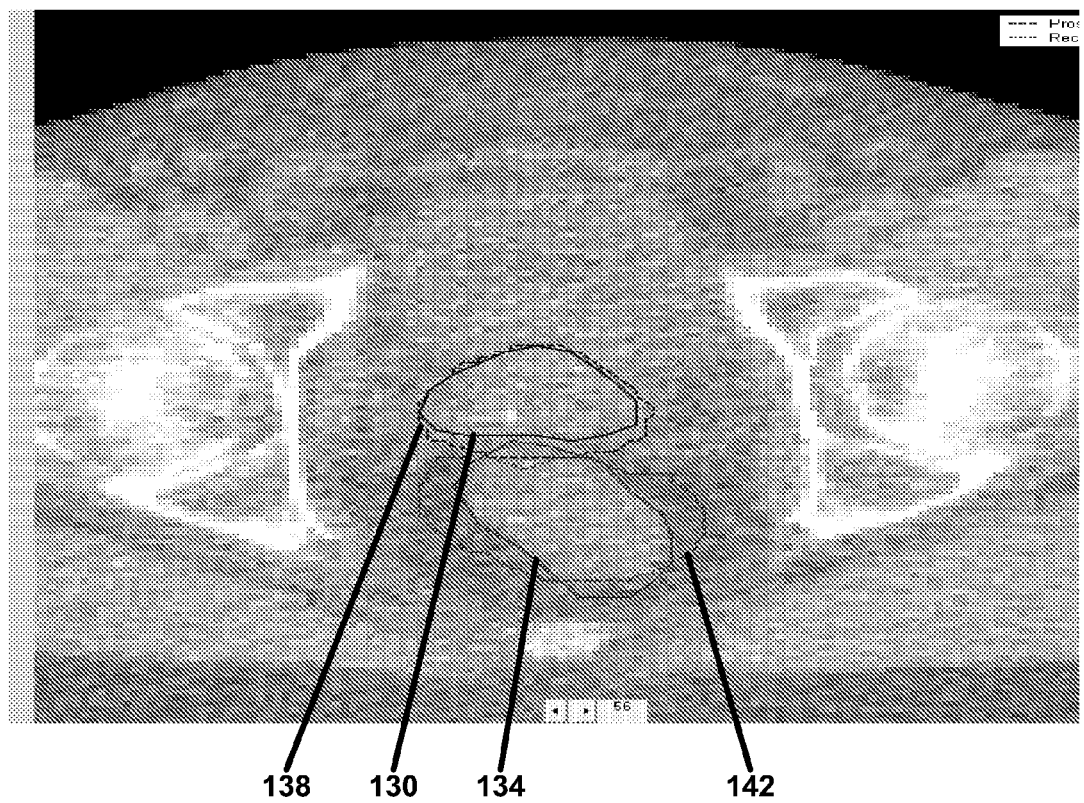
FIG. 8 is a resulting image of the patient including contours after applying the deformation map illustrated in FIG. 7.
Figure 9:
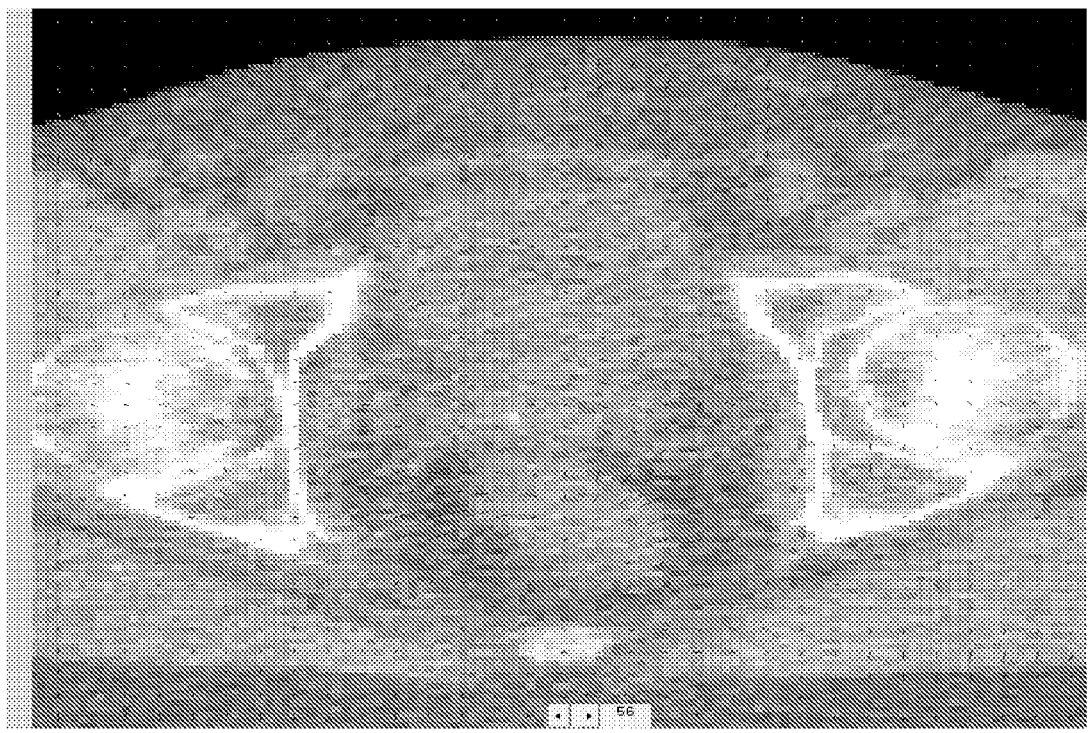
FIG. 9 is a deformation map using the manually-drawn contour of FIG. 6 as a constraint.
Figure 10:
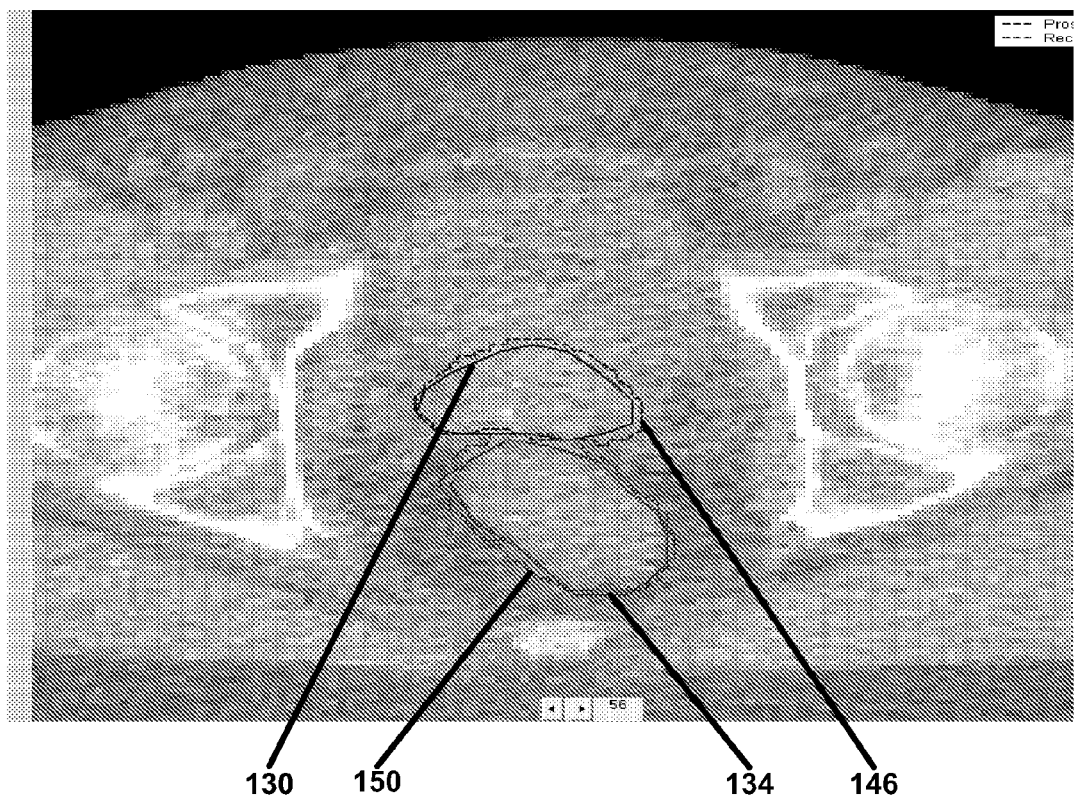
FIG. 10 is a resulting image of the patient including contours after applying the deformation map illustrated in FIG. 9.

The contour can be generated automatically or semi-automatically for a new image (e.g., a pre-treatment image). FIGS. 5-10 illustrate the use of a deformation map to apply contours from a planning image onto a newly-acquired image. This process begins with a planning or other baseline patient image that has an initial contour set. FIG. 5 illustrates a planning KVCT with a contour 122 around the prostate and a contour 126 around the rectum of a patient. When performing either quality assurance or adaptive therapy, it is common to have a new image, for which contours are not yet available. Rather than require medical personnel to manually contour the new image, it can be both faster and more consistent to perform a deformable image registration, and then use the deformation results as the basis for modifying the original contour set to reflect the new patient anatomy. FIG. 6 illustrates a pre-treatment image of the same patient illustrated in FIG. 5. The image includes a manually-drawn contour 130 around the prostate and a manually-drawn contour 134 around the rectum of the patient for purposes of evaluating automatically generated contours using deformable registration. FIG. 7 illustrates displacement vectors resulting from a deformable registration between the image in FIG. 5 and the image in FIG. 6. FIG. 8 illustrates an automatically generated contour 138 around the prostate and an automatically generated contour 142 around the rectum, and for comparison purposes, the manually-drawn contours 130 and 134 are also shown. Focusing on the rectum portion of the images, if the manually-drawn contour 134 is used as a constraint for the deformable registration then the resulting deformable registration between the image in FIG. 5 and the image in FIG. 6 is illustrated in FIGS. 9 and 10. A newly-added contour 146 (dashed line) around the prostate more closely resembles the manually-drawn contour 130. Similarly, a newly-added contour 150 (dashed line) around the rectum more closely resembles the manually-drawn contour 134. It is generally known that manual contours can suffer from irreproducibilities, whereas automatically generated contours can potentially be more consistent in applying the principles of an initial contour to the generation of subsequent contours.

A similar family of template-based contouring algorithms has been developed to generate contours for newly-available images, based upon previously available sets of images and contours. These template-based algorithms might contour a new patient image based upon a previous patient image and contour, or potentially based upon a canonical or atlas patient image and contour. This can be performed for adaptive therapy as a means to accumulate doses in daily images, each with automatic daily contours. It is an aspect of this invention to apply deformation-based contouring or template-based contouring to radiation therapy quality assurance and adaptive therapy. In this aspect, the invention applies these techniques to the particular wealth of image data and types of images that arise during image-guided radiation therapy. Specifically, this includes deformation and template-based contouring of multiple images of the same patient in which contour sets might only exist for one of the images. These multiple images of the patient may arise from use of an on-line or in-room patient imaging system, with images potentially taken on different days, or these images might derive from a "4D" imaging system such as a CT scanner, in which each image represents a phase of motion, such as a breathing phase. It should also be noted that the on-line or in-room imaging system might be the same, a similar, or a different modality from the reference image. For example, the reference image might be a CT image, whereas the on-line image could be a CT image, a cone-beam CT image, a megavoltage CT image, a MRI image, an ultrasound image, or an image generated by a different system or device. By porting these contouring techniques to the applications of quality assurance and adaptive therapy, it is possible to both save a considerable amount of time from the contouring of images, and this method can also improve the consistency of contours across multiple images of the same patient (taken at different times or representing different phases).

Another benefit of this process is that the contours generated provide a validation of the deformation process. If the generated contours closely reflect contours that one would manually draw, then it is a good indication that the deformation process is reasonable; whereas if the automatic contours are less relevant, it indicates to the medical personnel that perhaps the deformation is inappropriate, but also provides the medical personnel an opportunity to verify the manual contours to check for mistakes or inconsistencies. Another aspect of this invention is that the deformation-based contours can be used as a rough-draft of the contours for the adaptive process, and manually edited to reflect the desired contours for the on-line images. When doing this, the deformation process can then be re-run, constraining the deformation map to match the initial contours to the manually-edited automatic contours, and this helps direct consistent results through the rest of the image.

While the deformation process above was described in the context of registering one image to another image, it can also work with deformably registering a set of two or more images with another set of one or more images. For example, if there are two pairs of images, each pair comprising an MRI and a CT image, then the deformation map can register the two MRI images together in regions where the MRI has more information, and the CT images together where the CT has more information. These deformations could then be combined. Or deformation maps between the images could be used together, such as for using the CT deformation maps to correct for geometric distortion, imperfections, and/or incompleteness in the MRI images and deformations, and then, having corrected that distortion, imperfection, and/or incompleteness using the MRI deformation maps for better analysis of soft-tissue motion. In a general sense, this process enables imaging improvement via deformation, as poor images can be better understood, and therefore improved, by applying deformation techniques that indicate information like anatomical sizes, shapes, and content. This information can be incorporated into image reconstruction, modification, or enhancement processes.

The software program 90 also includes a treatment delivery module 154 operable to instruct the radiation therapy treatment system 10 to deliver radiation therapy to the patient 14 according to the treatment plan. The treatment delivery module 154 can generate and transmit instructions to the gantry 18, the linear accelerator 26, the modulation device 34, and the drive system 86 to deliver radiation to the patient 14. The instructions coordinate the necessary movements of the gantry 18, the modulation device 34, and the drive system 86 to deliver the radiation beam 30 to the proper target in the proper amount as specified in the treatment plan.

The treatment delivery module 154 also calculates the appropriate pattern, position, and intensity of the radiation beam 30 to be delivered, to match the prescription as specified by the treatment plan. The pattern of the radiation beam 30 is generated by the modulation device 34, and more particularly by movement of the plurality of leaves in the multi-leaf collimator. The treatment delivery module 154 can utilize canonical, predetermined or template leaf patterns to generate the appropriate pattern for the radiation beam 30 based on the treatment parameters. The treatment delivery module 154 can also include a library of patterns for typical cases that can be accessed in which to compare the present patient data to determine the pattern for the radiation beam 30.

Figure 11:
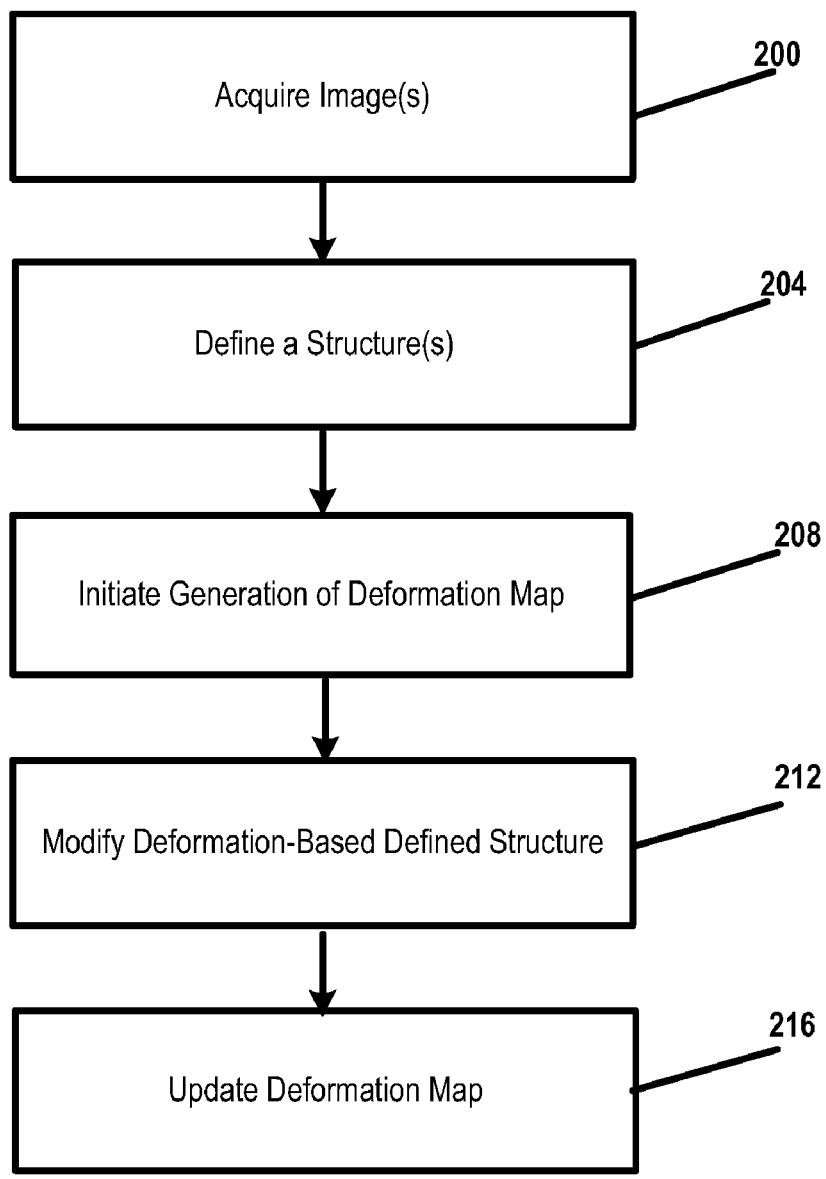
FIG. 11 is a flow chart of a method of placing constraints on a deformation map according to one embodiment of the present invention.

FIG. 11 illustrates a flow chart of a method of placing constraints on a deformation map. Medical personnel initiate acquisition (at 200) of one or more images (e.g., a planning image) of at least a portion of the patient 14. Next, medical personnel identify or define (at 204) one or more structures in the one or more images of the patient 14 using one or more contours or other identification tools. The defined structure is typically a target 38 in the one or more images. The medical personnel initiate (at 208) the generation of a deformation map between two or more of the previously acquired images with the deformation module 114 to relate the defined structure from the one image onto the other image to create a deformation-based defined structure. The medical personnel can modify (at 212) the deformation-based defined structure and initiate (at 216) the deformation module 114 to update the deformation map based on the modified deformation-based defined structure.

Figure 12:
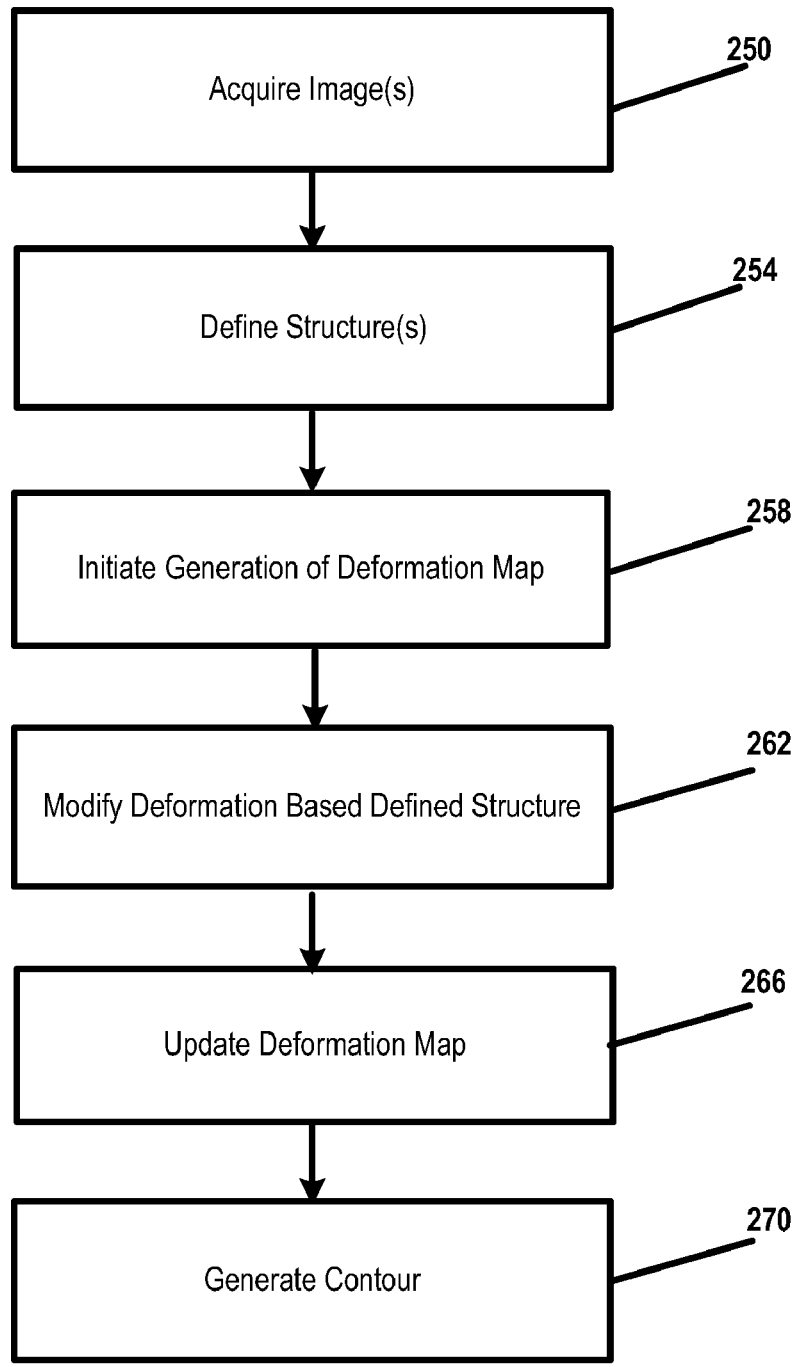
FIG. 12 is a flow chart of a method of placing constraints on a deformation map according to one embodiment of the present invention.

FIG. 12 illustrates a flow chart of a method of placing constraints on a deformation map. Medical personnel initiate acquisition (at 250) of one or more images (e.g., a planning image) of at least a portion of the patient 14. Next, medical personnel identify or define (at 254) one or more structures in the one or more images of the patient 14 using one or more contours or other identification tools. The defined structure is typically a target 38 in the one or more images. The medical personnel initiate (at 258) the generation of a deformation map between two or more of the previously acquired images with the deformation module 114 to relate the defined structure from the one image onto the other image to create a deformation-based defined structure. The medical personnel can modify (at 262) the deformation-based defined structure and initiate (at 266) the deformation module 114 to update the deformation map based on the modified deformation-based defined structure. Based on the updated deformation map, the contour module 118 generates (at 270) a contour on one of the images.

Figure 13:
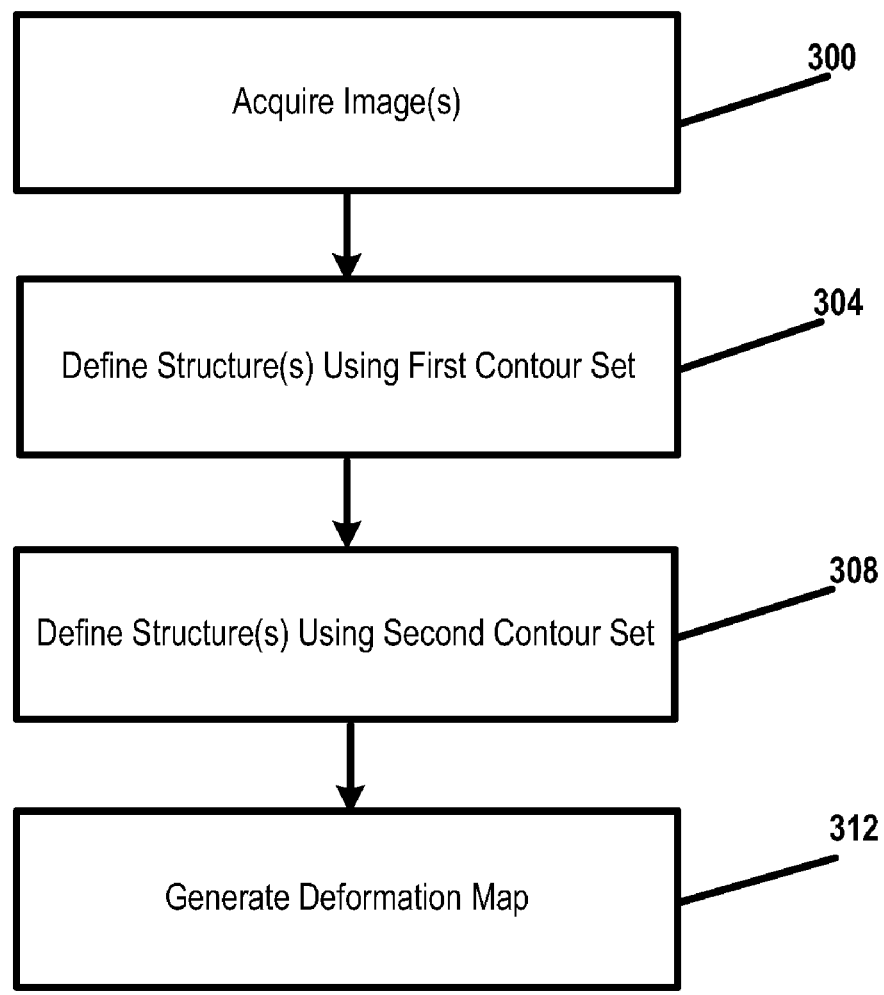
FIG. 13 is a flow chart of a method of placing constraints on a deformation map according to one embodiment of the present invention.

FIG. 13 illustrates a flow chart of a method of placing constraints on a deformation map. Medical personnel initiate acquisition (at 300) of one or more images (e.g., a planning image) of at least a portion of the patient 14. Next, medical personnel identify or define (at 304) one or more structures in the one or more images of the patient 14 using a first contour set or other identification tools. The defined structure is typically a target 38 in the one or more images. Medical personnel identify or define (at 308) or further define one or more structures in the one or more images of the patient 14 using a second contour set or other identification tools. The medical personnel initiate (at 312) the generation of a deformation map between the first contour set and the second contour set to identify the differences between the contour sets.

Various features and advantages of the invention are set forth in the following claims.

What is claimed is:

1. A method of placing constraints on a deformation map, the method comprising using a computer to carry out the steps of:
    generating a deformation map between two images;
    identifying a defined structure in one of the images;
    applying the deformation map to relate the defined structure from the one image onto the other image to create a deformation-based defined structure;
    independently generating a contour around at least a portion of the deformation-based defined structure;
    modifying the deformation-based defined structure; and
    updating the deformation map in response to the step of modifying the deformation-based defined structure.

2. A method as set forth in claim 1 wherein modifying the deformation-based defined structure is performed manually.

3. A method as set forth in claim 1 wherein the method of placing constraints on a deformation map is performed during planning and delivery of a radiotherapy treatment plan.

4. A method as set forth in claim 1 wherein the images are computer-generated images of at least a portion of a patient, the computer-generated images being acquired using a medical imaging device.

5. A method as set forth in claim 1 and further comprising generating a contour based on the updated deformation map.

6. A method as set forth in claim 1 and further comprising determining a dose accumulation in the patient based on the deformation map.

7. A method as set forth in claim 1 further comprising the act of remapping one of the images based on the deformation map.

8. A method as set forth in claim 1 further comprising generating a new image by applying the deformation map to one of the images.

9. A method as set forth in claim 1 further comprising combining the two images and the deformation map to generate a new image.

10. A method as set forth in claim 1 wherein the images are generated from different imaging modalities.

11. A method as set forth in claim 1 wherein the images are based on a time-series set of volumes.

12. A method of placing constraints on a deformation map, the method comprising using a computer to carry out the steps of:
    generating a deformation map between two images;
    identifying a defined structure in one of the images;
    applying the deformation map to relate the defined structure from the one image onto the other image to create a deformation-based defined structure;
    independently generating a contour around at least a portion of the deformation-based defined structure;
    modifying the deformation-based defined structure;
    updating the deformation map in response to the step of modifying the deformation-based defined structure; and
    generating a contour based on the updated deformation map.

13. A method as set forth in claim 12 wherein modifying the deformation-based defined structure is performed manually.

14. A method as set forth in claim 12 wherein the method of placing constraints on a deformation map is performed during planning and delivery of a radiotherapy treatment plan.

15. A method as set forth in claim 12 wherein the images are computer-generated images of at least a portion of a patient, the computer-generated images being acquired using a medical imaging device.

16. A method as set forth in claim 12 and further comprising determining a dose accumulation in the patient based on the deformation map.

17. A method as set forth in claim 12 further comprising remapping one of the images based on the deformation map.

18. A method as set forth in claim 12 further comprising generating a new image by applying the deformation map to one of the images.

19. A method as set forth in claim 12 wherein the images are generated from different imaging modalities.

20. A method as set forth in claim 12 wherein the images are based on a time-series set of volumes.

21. A method of placing constraints on a deformation map, the method comprising using a computer to carry out the step of:

generating a first contour set of a first region of interest in a first image;

generating a second contour set after generating the first contour set of a second region of interest in a second image;

generating a deformation map between the first image and the second image after the first contour set and the second contour set are generated;

constraining the deformation map such that the first region of interest in the first image maps to the second region of interest in the second image; and using the deformation map to accumulate dose delivered to the patient.

22. A method as set forth in claim 21 wherein one of the first contour set and the second contour set includes an image.

23. A method as set forth in claim 22 wherein the images are computer generated images of at least a portion of a patient, the computer generated images being acquired using a medical imaging device.

24. A method as set forth in claim 22 further comprising generating a new image by applying the deformation map to one of the images.

25. A method as set forth in claim 22 wherein the images are generated from different imaging systems.

26. A method as set forth in claim 22 wherein the images are based on a time-series set of volumes.

27. A method as set forth in claim 21 wherein the method of placing constraints on a deformation map is performed during planning and delivery of a radiation therapy treatment plan.

28. A method as set forth in claim 21 wherein the first contour set defines a first region of interest and wherein the second contour set defines a second region of interest and further comprising applying the deformation map to relate the first region of interest onto the second region of interest to create a deformation-based defined region of interest.

29. A method as set forth in claim 28 and further comprising modifying the deformation-based defined region of interest.

30. A method as set forth in claim 1 further comprising displaying the deformation map on a display and manually generating a contour.

* * * * *